United States Patent [19]
Vetter et al.

[11] Patent Number: 5,808,076
[45] Date of Patent: Sep. 15, 1998

[54] ORALLY ADMINISTRABLE FORMULATIONS OF QUINOLONE- OR NAPHTHYRIDONECARBOXYLIC ACIDS

[75] Inventors: Oliver Vetter, Burscheid; Reinhold Löhr, Bergisch Gladbach; Matthias Kuhn, Monheim; Hubert Rast, Leverkusen; Martin Scheer, Wuppertal; Ernst Heinen, Echternacherbruück, all of Germany; Francisco Cabrera, Overland Park, Kans.

[73] Assignee: Bayer Aktiengesellschaft, Leverkusen, Germany

[21] Appl. No.: 761,687

[22] Filed: Dec. 6, 1996

[30] Foreign Application Priority Data

Aug. 20, 1996 [DE] Germany ............... 196 33 480.2

[51] Int. Cl.$^6$ ............... C07D 215/16; A61K 31/47
[52] U.S. Cl. ............... 546/156; 546/123; 514/312; 514/300
[58] Field of Search ............... 546/146, 156, 546/147, 123; 544/32, 64, 101; 514/254, 312

[56] References Cited

U.S. PATENT DOCUMENTS 5,202,337  4/1993  Peterson et al. ............... 514/312
5,281,596  1/1994  Kitao et al. ............... 514/254

FOREIGN PATENT DOCUMENTS 0 238 814   9/1987  European Pat. Off. .
0 209 000   8/1990  European Pat. Off. .
35 25 335.9 1/1987  Germany .

*Primary Examiner*—Bernard Dentz
*Assistant Examiner*—Charanjit S. Aulakh
*Attorney, Agent, or Firm*—Sprung Kramer Schaefer & Briscoe

[57] ABSTRACT

The present invention relates to the preparation of orally administrable formulations of quinolone- or naphthyridonecarboxylic acids by mixing quinolone- or naphthyridonecarboxylic acids as such or in the form of their water-soluble salts or derivatives, preferably in the form of their aqueous salt solutions, with embonic acid as such or in the form of its water-soluble salts or derivatives, preferably in the form of its aqueous salt solutions, in the presence of an excipient, optionally in the presence of auxiliaries, when using dry mixtures in the presence of water, and optionally converting the mixture obtained into further ready-to-use forms.

9 Claims, No Drawings

ORALLY ADMINISTRABLE FORMULATIONS OF QUINOLONE- OR NAPHTHYRIDONECARBOXYLIC ACIDS

The present invention relates to the preparation of orally administrable formulations of quinolone- or naphthyridonecarboxylic acids and formulations prepared by this process.

Embonates of quinolonecarboxylic acids are already known, for example from EP-A (European Published Specification) 238 814. They are used for preparing compositions in which the bitter taste of the active quinolone compounds is masked by salt formation with embonic acid. However, for preparing these compounds the embonates of quinolonecarboxylic acid first have to be prepared, then isolated and purified and subsequently formulated.

It has now been found that orally administrable formulations of quinolone- or naphthyridonecarboxylic acids can be obtained by mixing quinolone- or naphthyridonecarboxylic acids as such or in the form of their water-soluble salts or derivatives, preferably in the form of their aqueous salt solutions, with embonic acid as such or in the form of its water-soluble salts or derivatives, preferably in the form of its aqueous salt solution, in the presence of an excipient, optionally in the presence of auxiliaries, when using dry mixtures in the presence of water, and optionally converting the mixture obtained into further ready-to-use forms.

The process according to the invention produces a formulation containing quinolone- or naphthyridonecarboxylic acids which can be administered orally without any problems even to animals which will normally refuse formulations containing quinolone- or naphthyridonecarboxylic acid owing to their bitter taste.

For preparing the formulation, it is not necessary to prepare and isolate the embonic acid salt of the active compounds first and then to apply these salts to the excipient. Surprisingly, it was sufficient for preparing the formulation according to the invention to mix active compound and embonic acid or its salts and derivatives separately or together in the presence of water with the excipient to give a formulation. It was further surprising that the thus-prepared formulation was taken up orally without any hesitation even by taste-sensitive animals. This was not to be expected, since it is not clear if the embonic acid salts are formed completely, in part or not at all in the process according to the invention. What is decisive is that a formulation is formed which has an outstanding acceptance when administered orally and which comprises the following components:

excipient,
quinolone- or naphthyridonecarboxylic acids, their salts or derivatives,
embonic acid, its salts or derivatives.

Quinolone- or naphthyridonecarboxylic acids and their water-soluble salts and derivatives are known, for example from EP-A (European Published Specification) 350 950, 302 372, 49 355, 47 005, 242 789, 259 804, 215 650, 131 839, 109 284; DE-A (German Published Specification) 2 804 097; FR-P (French Patent Specification) 2 463 771; PCT WO 92/9596. (The formulae and the specific compounds mentioned in these publications are incorporated herein by reference.)

Preferred compounds are:
temafloxacin, tosufloxacin, enrofloxacin, ciprofoxacin, ofloxacin, orbifloxacin, marbofloxacin, norfloxacin, benofloxacin, binfloxacin, danofloxacin, difloxacin, sarafloxacin, premafloxacin, ibafloxacin.

Particularly preferred compounds are:
enrofloxacin, danofloxacin, sarafloxacin.

Derivatives of these active compounds include their esters such as the $C_1$–$C_4$-alkyl esters.

Salts of these active compounds include all salts with acids forming physiologically acceptable salts. These include hydrohalic acids, sulfonic acids, carboxylic acids, amino acids, (poly)-hydroxycarboxylic acids, phosphonic acid, nitric acid, sulfuric acid. Specifically, these are methanesulfonic acid, ethanesulfonic acid, hydroxyethanesulfonic acid, benzenesulfonic acid, p-toluenesulfonic acid, formic acid, acetic acid, propionic acid, dimethylolpropionic acid, hydroxyacetic acid, lactic acid, hydroxymaleic acid, oxalic acid, succinic acid, fumaric acid, maleic acid, glutaric acid, malonic acid, adipic acid, ascorbic acid, malic acid, citric acid, tartaric acid, aminosalicyclic acid, anthranilic acid, benzoic acid, hydroxybenzoic acid, phenylacetic acid, salicylic acid, phthalic acid, nicotinic acid, mandelic acid, aspartic acid, glutamic acid, gluconic acid, glucuronic acid, latobionic acid, galaturonic acid, mucic acid, phosphoric acid, nitric acid, hydrochloric acid, sulfuric acid, 5-oxotetrahydrofuran-2-carboxylic acid, 2-hydroxyglutaric acid.

Very particularly preference is given to hydrochloric acid or gluconic acid.

Embonic acid and its salts are known, for example from The Merck Index, 10th edition, Ref. 6867.

Suitable bases for forming salts with embonic acid are, for example, the following:
alkali metal and alkaline earth metal hydroxides, such as KOH, NaOH, $Ca(OH)_2$, ammonia, basic amino acids such as arginine, lysine, choline, N-methylglucamine, ethylenediamine, mono-, di-trialkylamines, substituted amines such as, for example, diethanolamine, cyclic amines such as, for example, morpholine, piperazine, tromethamol (=tris(hydroxymethyl)aminomethane).

Particularly suitable are KOH, arginine, lysine, N-methylglucamine.

Suitable excipients for the formulations according to the invention are all solid inert substances.

Inorganic and organic substances may be used in this capacity.

Examples of inorganic substances are: common salt, carbonates (for example calcium carbonic), hydrogencarbonates, aluminum oxides, silicas, clays, precipitated or colloidal silicon dioxide, phosphates.

Examples of organic substances are: sugar, cellulose, optionally their derivatives, starches (for example corn, rice, potato, tapioca or wheat starch), foodstuff and feeds such as, for example, milk powder, animal meal, ground and bruised grain.

The carrier used may also be a mixture of the substances mentioned.

Further carriers, which in addition have the property of binding water, are for example carboxymethyl cellulose, methyl cellulose and other cellulose and starch derivatives, polyacrylates, alginates, gelatin, chitin, gum arabic, polyvinylpyrrolidone, polyvinyl alcohols, copolymers of vinyl ether and acid anhydrides, polyethylene glycols, waxes, colloidal silicas or mixtures of the substances and classes of substances mentioned.

To prepare the formulations according to the invention, other auxiliaries such as preservatives, antioxidants, photostabilizers, colorants, absorption-promoting substances, disintegration-promoting substances, binders or lubricants and stabilizers may be added.

Suitable preservatives are, for example, benzyl alcohol, benzoic acid, p-hydroxybenzoic acid, propionic acid and its derivatives and salts and also sorbic acid and its derivatives and salts.

Suitable antioxidants are, for example, albumins; amino acids, ascorbic acid, its salts and derivatives; butylhydroxyanisole; butylhydroxytoluene; derivatized hydroquinones.

Suitable photostabilizers are, for example, derivatives of aromatics, compounds with a suitable absorption wavelength.

Suitable colorants are, for example, pigments, such as, for example, iron pigments, water-soluble colorants or colorants soluble in organic solvents.

Suitable absorption-promoting substances are, for example, fatty acid, fatty acid esters and mixtures thereof, fatty alcohols, lecithin, bile acid salts.

Suitable stabilizers are, for example, sodium sulfite, EDTA and its salts.

Suitable lubricants are, for example, magnesium stearate, stearic acid, talc, bentonites; suitable disintegration-promoting substances are, for example, starch or cross-linked polyvinylpyrrolidone, suitable binders are, for example, starch, gelatine or linear polyvinylpyrrolidone and also dry binders such as microcrystalline cellulose.

The process according to the invention is carried out by mixing the individual components in the presence of water. The order in which the components are added is not crucial.

Thus, the excipient and auxiliary components can be charged initially in a conventional mixer and mixed. To this mixture, active compound is added as such or in the form of its water-soluble salts or derivatives, preferably in the form of its aqueous salt-solution, and mixed. The thus-obtained mixture is then admixed with embonic acid as such or in the form of its water-soluble salts or derivatives, preferably in the form of its aqueous salt solution, and mixed, when using dry mixtures in the presence of water.

For preparing the aqueous solutions, the addition of water-miscible solvents and auxiliaries may be useful.

Examples of such additives include:
propylene glycol, ethanol, isopropyl alcohol, acetone, N-methylpyrrolidone, 2-pyrrolidone, chlorobutanol, benzyl alcohol, preservatives, stabilizers such as Na sulfite, Na-EDTA, colorants, viscosity-increasing substances such as polyvinylpyrrolidone, cellulose derivatives, gelatin, starch glue.

The concentration of the active compound (salt) solution is from 0.5 to 50%; preferably 10 to 40%.

The concentration of the embonic acid (salt) solution is from 0.5 to 40%; preferably 5 to 30%.

The ratio of active compound to embonic acid in the product prepared according to the process described, is, when using 1 mol of active compound, 0.5 to 5 mol of embonic acid, preferably 0.7 to 2 mol, more particularly 1 mol of embonic acid.

The individual components can be mixed in any type of mixer. For example, high intensity mixers having chopping devices are particularly suitable for preparing a homogeneous mixture. The solutions employed or water are added to the dry mixture in any order, including alternately, continuously or batchwise, by tipping, pouring, spraying or atomizing.

The moist mixture is processed further and, for example, grated, dried, then, for example, sieved or ground.

Likewise, granulation using the fluidized-bed process is a suitable method of preparation. For this purpose for example the solutions are sprayed onto the moving mixture using one or more nozzles and, if desired, dried in the process.

If particularly small particles are required, micronizing may be an option (for example by using an air impact, bead or trituration mill).

The formulations prepared according to the invention can be admixed with other excipients, in foodstuff applications these can be for example single feeds or mixtures thereof. Such formulations can be extruded or pelletized in powder form, dry or moist.

The formulations according to the invention can be applied dry on food pellets. The addition of a binder may be useful. Suitable binders are, for example, vegetable, animal or synthetic oils, fats, fatty acids, fatty alcohols, waxes, gelatine.

The formulations prepared according to the invention can also be incorporated into moist pellets. Such pellets may comprise animal matter (for example moist pellet).

The formulations prepared according to the invention can, inter alia, also be filled into capsules, the capsule wall being made of hard or soft gelatin. The capsule can, if appropriate, be enteric-coated.

The formulations prepared according to the invention can also be used for preparing other orally administrable formulations, such as oral solutions, concentrates for oral administration after dilution;

emulsions and suspensions for oral administration;

pastes or preparations in which the formulation is processed in a semi-solid base or in an oil-in-water or water-in-oil emulsion base;

solid preparations such as powders, premixes or concentrates, pellets, extrudates, tablets, boluses, capsules;

or combinations of the forms mentioned.

The formulations prepared by the process according to the invention can be used as such or in a formulation adapted to the prophylaxis or therapy of diseases in humans or target animals, in particular the treatment of bacterial infections.

They are especially suitable for use in the fields of geriatrics and pediatrics or in veterinary practice in taste-sensitive animals, such as, for example, cats, pigs or fish.

The formulations are active against microorganisms pathogenic to humans and animals.

These microorganisms include:
1. *Spirochaetaceae* (for example *Treponema, Leptospira, Borrelia*)
2. *Spirillaceae*
3. *Micrococcaceae* (for example *staphylococci* of biotype A-F, *St. hyicus*)
4. *Streptococcacease* (for example *Streptococcus uberis. Str. Equi. Str. agalactiae, Str. dysgalactiae, streptococci* of the Lancefield groups A–N)
5. *Pseudomonaceae* (for example *Pseudomonas malei, Ps. cepacia, Ps. aeruginosa, Ps. maltophilia*), *Brucella,* such as *Brucella abort, B. melitensis, B. suis, Bordetella,* such as *Bordetella bronchiseptica, Moraxella, Acinetobacter*)
6. *Enterobacteriaceae* (for example *Salmonella* of the types B–E, *Shigella, E. coli, Klebsiella, Proteus, Citrobacter, Edwardsiella, Haemophilus, Providencia, Yersina*)
7. *Vibronaceae* (for example *Bribrio* such as *Vibrio chloerae*), *Pasteurella* such as *Pasteurella multocia, Aeromonas, Actinobacillus, Streptobacillus*)
8. *Bacteroidaceae* (for example *Bacteroides, Fusobacterium*)
9. *Erysiphylothix, Listeria* such as *Listeria monocytojenes*
10. *Bacillaceae* (for example *Bacillus, Closteridium* types A–D, such as *Clostridium perfringens*), *Lactobacillaceae* and also anaerobic cocci such as, for example, *Peptostreptococci* and *Peptococci*
11. coryneform bacteria (for example *Corynebacterium pyogenes*)
12. *Mycobacteriaceae* (for example *Mycobacterium bovis, M. avium, M. tuberculosis*)

13. *Actinomyceae* (for example *Actinomyces bovis, A. israelii*)
14. *Nocardiaceae* (for example *Norcardia facinica, N. asteroides*)
15. *Rickettsjaceae* (for example *Coxiella, Rickettsia*)
16. *Bartonellaceae* (for example *Baronella*)
17. *Chlamydiaceae* (for example *Chlamydia psittaci*)
18. *Mycoplasmataceae* (for example *Mycoplasma mycoides, M. agalactiae, M. gallisepticum*)

Microorganisms pathogenic to humans and animals can cause disease symptoms in mono- or mixed infections of the following animal organ systems:

lungs and intratracheal lumen, digestive systems such as stomach and intestine, breast and udder, genital system such as uterus, soft tissue such as skin, muscles, nails, claws, hoofs, active and passive locomotive system such as bones, muscles, sinews, joints, urogenital system such as kidney, urethra, ureter, nervous system, ears, eyes, gills.

As already mentioned, the formulations are used to fight bacterial diseases in humans and animals. The animals include:

mammals, such as, for example, cattle, horses, pigs, sheep, goats, dogs, cats, camels, for animals such as mink, chinchilla, zoo animals and laboratory animals such as, for example, mice and rats;

birds, such as, for examples, geese, chickens, turkeys, ducks, pigeons, aviary birds, laboratory birds, such as, for example, parrots and budgerigars;

fish, in particular economically useful fish, such as, for example, carp, trout, salmon, tench, eels, Yellow tails, sea bass, sea bream, furthermore ornamental fish and aquarium fish;

reptiles, such as, for example, crocodiles, snakes, frogs;

crustaceans, such as, for example, *Penaeidae;* for example *P. monodon,* crabs, lobsters.

The bacterial diseases of animals include swine dysentery, spirochactosis in fowl, leptospirosis in cattle, swine, horses, dogs: *Campylobacter*-induced enteritis in cattle; *Campylobacter*-induced abortion in sheep and swine; *Campylobacter*-induced hepatitis in chicken, infections of the skin; pyoderma in dogs, otitis externa; mastitis in cattle, sheep and goats; streptococcal mastitas, streptococcal infections of the horse, of pigs and other kinds of animals; pneumococcal infections of the calf, and of other kinds of animals; glanders; conjunctivitis; enteritis; pneumonia; brucellosis in cattle, sheep, swine; stropic rhinitis of swine; salmonellosis in cattle, horses, sheep, chicken and other kinds of animals; septicemia; *Escherichia coli* infections in piglets; metritis-mastitis-agalactic-(MMA)-syndrome; *Klebsiella* infections; pseudotuberculosis; contagious pleuropneumonia; primary pasteurelloses; foal ataxia; necrobacillosis in cattle and pets; leptospirosis; erysipelas of swine and other kinds of animals; listeriosis; anthrax; clostridioses; tetanus infections; botulism; infections with *Corynebacterium pyogenes;* tuberculosis in cattle, swine, fowl and other kinds of animals; paratuberculosis of the ruminants; nocardiosis; Q fever; ornithosis-psittacosis; encephalomycelitis; mycoplasmosis of cattle and other animals, porcine enzootic pneumonia.

In fish, bacterial diseases include:

bacterial kidney diseases (caused by *Renibacterium Salmoniarum*); streptococcoses, *Pseudomonas* infections, for example *P. Fluorescens, P. anguiliceptica; Edwardsiella* infections, for example *E. tarda; Aeromonas* infections, for example *A. Salmonicida (furuneulosis), A. hydrophila; vibroses,* for example *V. anguillarum, V. salmonicida; Vibrio parahaemolyticus; Bacillus culumnaris; rickettsioses,* for example SRS.

Bacterial infections in crustaceans include:

*vibrioses,* such as, for example, *Vibrio parahaemolytieus, Vibrio alginolytieus; Pseudomonas* infections, such as, for example, *Pseudomonas* spp.

The process according to the invention provides the formulations below:

EXAMPLE 1

| Molar ratio enrofloxacin: embonic acid | Granulate a 1:1 | Granulate b 1:0.9 | Granulate c 1:1 | Granulate d 1:1.5 |
| --- | --- | --- | --- | --- |
| enrofloxacin | 10.00 | 10.00 | 2.500 | 2.500 |
| gluconolactone | 6.00 | 6.00 | 1.500 | — |
| methane-sulfonic acid | — | — | — | 0.670 |
| sodium sulfite | 0.10 | 0.10 | 0.025 | 0.025 |
| embonic acid | 10.82 | 9.74 | 2.705 | 4.057 |
| methyl-glucamine | 10.88 | — | 2.720 | 4.080 |
| arginine | — | 8.75 | — | — |
| -MHP-cellulose 50 | — | — | 1.500 | 1.500 |
| Ac-Di-Sol | 7.00 | 7.00 | — | — |
| corn starch moist ad (weight in g) | 100.0 | 100.0 | 100.0 | 100.0 |

The excipients and auxiliaries are fed into a mixer-granulator and mixed. The aqueous solution of the enrofloxacin-gluconolactone- or methanesulfonic acid is then added to the mixture initially charged. Subsequently, the aqueous solution of the embonic acid-arginine or methylglucamine salt is added to the mixture formed. The mixture is then dried in a suitable device (for example fluidized-bed dryer) and sieved (for example oscillating sieve).

The formulations obtained by the method of Example 1 can either be used as such or after grinding or be processed further to give formulations of the compositions below:

EXAMPLE 2

Tablet 15 mg

|  | % | mg/tablet |
| --- | --- | --- |
| Enrofloxacin granules 10% | 75.00 | 150.0 |
| Corn starch | 15.00 | 30.0 |
| Microcrystalline cellulose | 9.55 | 19.1 |
| Magnesium stearate | 0.30 | 0.6 |
| Colloidal silica | 0.15 | 0.3 |
|  |  | 200.0 |

EXAMPLE 3

Table 40 mg

|  | % | mg/tablet |
| --- | --- | --- |
| Enrofloxacin granules 10% | 80.00 | 400.00 |
| Corn starch | 10.00 | 50.00 |
| Microcrystalline cellulose | 9.55 | 47.75 |
| Magnesium stearate | 0.30 | 1.50 |
| Colloidal silica | 0.15 | 0.75 |
|  |  | 500.00 |

EXAMPLE 4

| Enrofloxacin suspension aqueous 2.5% | |
|---|---|
| Enrofloxacin granules 10% | 25.00 g |
| Benzyl alcohol | 1.40 g |
| Carboxymethyl cellulose-Na | 0.50 g |
| Demineralized water | ad 100 ml |

EXAMPLE 5

| Enrofloxacin suspension oily 2.5% | |
|---|---|
| Enrofloxacin granules 10% | 25.00 g |
| Benzyl alcohol | 1.40 g |
| Medium-chain triglycerides | ad 100 ml |

EXAMPLE 6

| Enrofloxacin paste 2.5% | |
|---|---|
| Enrofloxacin granules 10% | 25.00 g |
| Fatty alcohols | 5.00 g |
| Vaseline white | 10.00 g |
| Paraffin viscous | 60.00 g |
| | 100.00 g |

EXAMPLE 7

| Enrofloxacin gel 2.5% | |
|---|---|
| Enrofloxacin granules 10% | 25.00 g |
| 1,2-Propylene glycol | 10.00 g |
| Benzyl alcohol | 1.40 g |
| Carboxymethyl cellulose-Na | 2.50 g |
| Demineralized water | 61.10 g |
| | 100.00 g |

EXAMPLE 8

| Medihated feed 0.05% | |
|---|---|
| Enrofloxacin granules 10% | 0.5 g |
| Feed mixture/pellets | 99.5 g |
| | 100.00 g |

We claim:

1. A process for preparing an orally administrable formulation of a quinolone- or naphthyridonecarboxylic acid, said process comprising mixing the following components a)–c):
   a) a quinolone- or naphthyridonecarboxylic acid or a water-soluble salt or derivative thereof;
   b) embonic acid or a water-soluble salt or derivative thereof; and
   c) an excipient;
in any order, and without isolation of any embonates of said quinolone- or naphthyridonecarboxylic acid.

2. The process according to claim 1, wherein said components a)–c) are dry, and the process comprises mixing the components a)–c) with water in any order, and without isolation of any embonates of said quinolone- or naphthyridonecarboxylic acid.

3. The process according to claim 1, further comprising mixing the components a)–c) with an auxiliary in any order, and without isolation of any embonates of said quinolone- or naphthyridonecarboxylic acid.

4. The process according to claim 2, further comprising mixing the components a)–c) with water and an auxiliary in any order, and without isolation of any embonates of said quinolone- or naphthyridonecarboxylic acid.

5. The process according to claim 1, wherein said quinolone- or naphthyridonecarboxylic acid or water-soluble salt or derivative thereof is a water-soluble salt of enrofloxacin.

6. A granular product prepared by the process according to claim 2.

7. The granular product according to claim 6, wherein said quinolone- or naphthyridonecarboxylic acid or water-soluble salt or derivative thereof is a water-soluble salt or enrofloxacin.

8. A granular product prepared by the process according to claim 4.

9. The granular product according to claim 8, wherein said quinolone- or naphthyridonecarboxylic acid or water-soluble salt or derivative thereof is a water-soluble salt of enrofloxacin.

* * * * *